United States Patent [19]

Fry

[11] 3,954,619
[45] May 4, 1976

[54] SCUM DRAG

[76] Inventor: Lucius John Fry, 1223 N. Nopal St., Santa Barbara, Calif. 93103

[22] Filed: May 6, 1975

[21] Appl. No.: 574,856

[52] U.S. Cl. .............................. 210/242 S; 210/525
[51] Int. Cl.² ........................................ E02B 15/04
[58] Field of Search ............... 210/85, 242, DIG. 21, 210/525; 37/71, 117

[56] References Cited
UNITED STATES PATENTS

| 3,147,221 | 9/1964 | Johnston | 210/525 X |
| 3,756,418 | 9/1973 | Pentz et al. | 210/525 |
| 3,796,658 | 3/1974 | Meissner, Sr. | 210/242 |
| 3,872,005 | 3/1975 | Balter | 210/525 |
| 3,872,017 | 3/1975 | Bishop | 210/525 |

Primary Examiner—Theodore A. Granger
Attorney, Agent, or Firm—Harry W. Brelsford

[57] ABSTRACT

A scum drag for removal of floating scum from a closed methane generator is a float having a fence or rake extending upwardly. Draglines are connected to it to pull the float and fence in a direction transverse to the fence. The pile of scum that accumulates with movement is engaged by the fence and bodily moved to a scum exit, where it is discharged into a truck or otherwise transported away.

1 Claim, 2 Drawing Figures

SCUM DRAG

This invention relates to methane generators for rural gas supplies wherein animal manure is decomposed by anaerobic bacteria and has particular reference to a floating fence or drag for the occasional removal of a floating scum layer that forms on the liquid surface of the generator.

Methane gas generators may be used as a source of heating and illuminating gas in rural areas not serviced by utility pipelines. Animal manure is used as a raw material which is converted to methane gas and carbon dioxide under controlled conditions of temperature and pH by anaerobic bacteria. These bacteria function only in the complete absence of oxygen, and, accordingly, the digesters must be completely sealed from the atmosphere. For this reason, the usual skimmers used on municipal sewage treatment plants, which are open to the atmosphere, cannot operate in anaerobic digesters. The scum removal equipment for rural anaerobic digesters must be specially designed to remove the particular type of scum which results from the animal manure used as the raw material.

The raw material may be the manure from chickens, turkeys, hogs, goats, sheep, and horses, and the fresh manure from cattle. Such manure is scraped from the surface of the ground or pens or stalls and contains quantities of hair, straw, undigested cellulose, feathers, skin particles rubbed off in scratching, wood shavings from animal bedding, and other organic materials. These organic materials are not decomposed by the fermentation action of anaerobic bacteria and rise to the top of the liquid fermentation pool. Inorganic materials such as sand and gravel are removed by floating a slurry of manure and water through a sand trap, prior to flowing the slurry into the digester.

The scum of hair, feathers, straw, etc., forms a floating mat on the liquid of the digester. As more manure slurry is added at regular intervals, the amount of material in the floating scum increases. Depending upon the type and quality of manure used, the scum must be removed every 6 months or year and the mat of hair, feathers, etc., may be from 4 to 18 inches in thickness. While the mat of scum materials is porous, it eventually interferes with methane generation and must be removed.

The scum is bound together in matted form by fine particles of sticky materials brought up from the liquid pool which is continuously agitated by the fermentation or bacterial action of the anaerobic bacteria. This floating mass can be broken up by mechanical agitation, but this is not effective to improve methane production, because the scum layer quickly re-forms. The only effective treatment, in my experience, to maintain methane efficiency is removal of the scum mass. While this can be done by hand or hoes or hand rakes, this is expensive and is highly dangerous as the methane atmosphere must be flushed out so that workers can enter the digester.

I have discovered that an effective scum rake or drag can be constructed and kept permanently inside the digester. It is preferably actuated by power, and pulling by a truck or tractor is satisfactory. Rather than provide rails and rollers, I have found that the rake can be floating on the fermentation liquid and will operate effectively on the scum, because it is at the same level as the scum. In summary, I provide a floating drum upon which a screen or fence is erected to act as a rake. This screen is preferably transverse to the greatest dimension of the digester enclosure and is pulled to one end and in a direction transverse to the fence or rake. The mass of scum pulled to that end then slides out a scum door to be hauled away.

DESCRIPTION OF THE FIGURES

Various objects, advantages, and features of the invention will be apparent in the following description and claims considered together with the drawings forming an integral part of this specification, and in which:

Referring to FIG. 1, there is illustrated a methane generator 10 which includes an outer shell in cylindrical form; for example, a steel shell 100 feet long and 25 feet in diameter. This shell 11 has closed ends in which are disposed scum-removal openings 12 and 13, respectively. The methane is formed from a slurry of manure and water, which is introduced at a slurry inlet 14, which falls into the shell 11 to form a liquid pool 16 in which bacteria act upon the manure. The methane generated exits through a gas outlet tube 17. From time to time the liquid is removed by means of a liquid outlet 18, so that the level of the pool 16 is maintained at a fixed level as regular amounts of slurry are introduced at inlet 14.

Figure 1:
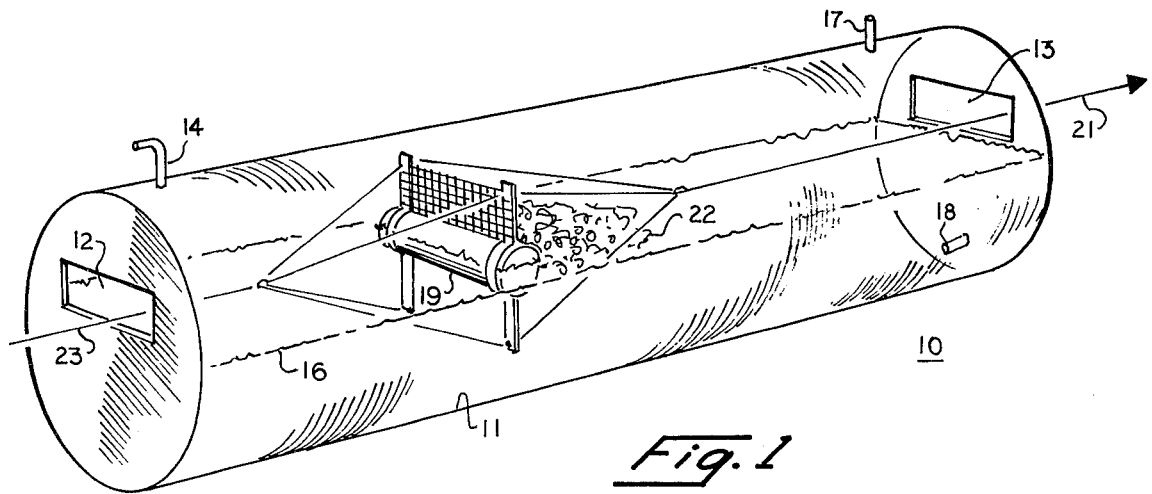
FIG. 1 is a three-dimensional phantom view of a methane generator in which is disposed a scum drag embodying the invention.

During the course of operation for several months as slurry is introduced into the inlet 14 daily or at other regular intervals, the nature of the manure causes a scum 22 to form on the liquid pool 16. When it is desired to remove this scum, the doors (not shown) are removed from the left-hand end, as seen in FIG. 1, to create the scum opening 12 and from the right-hand end, as seen in FIG. 1, to create the opening 13. These doors are normally sealed gas-tight to prevent the escape of methane gas. A dragline 21 connected to the scum drag 19 is then pulled to the right as shown in FIG. 1 to move the entire mass of scum 22 to the right where it will exit through the scum opening 13. If it is desired to return the scum drag 19 to the left-hand end of the shell 11, as shown in FIG. 1, then a second dragline 23 is pulled to the left to return the drag to the left-hand end. The drag can be operated alternately to remove the scum through either opening 12 or 13, but generally an apron or other structure is created at one of the openings so that it is more desirable to move the scum in one direction only.

During gas generation the openings 12 and 13 are normally sealed as mentioned previously and the liquid level in the shell 11 is maintained above the center point of the shell. The scum width, accordingly, is less than the diameter of the shell 11. The scum drag 19 floats at a level higher than that illustrated in FIG. 1, and for this reason its transverse dimension is less than the diameter of the shell 11 and its vertical dimension is preferably closer to one-half of the diameter. The level of the liquid shown in FIG. 1 is used only when it is desired to remove the scum, and this level is maintained at close to the scum exit 13 so that the scum will be easily pushed through the opening to be dumped into a truck or otherwise removed from the area.

Figure 2:
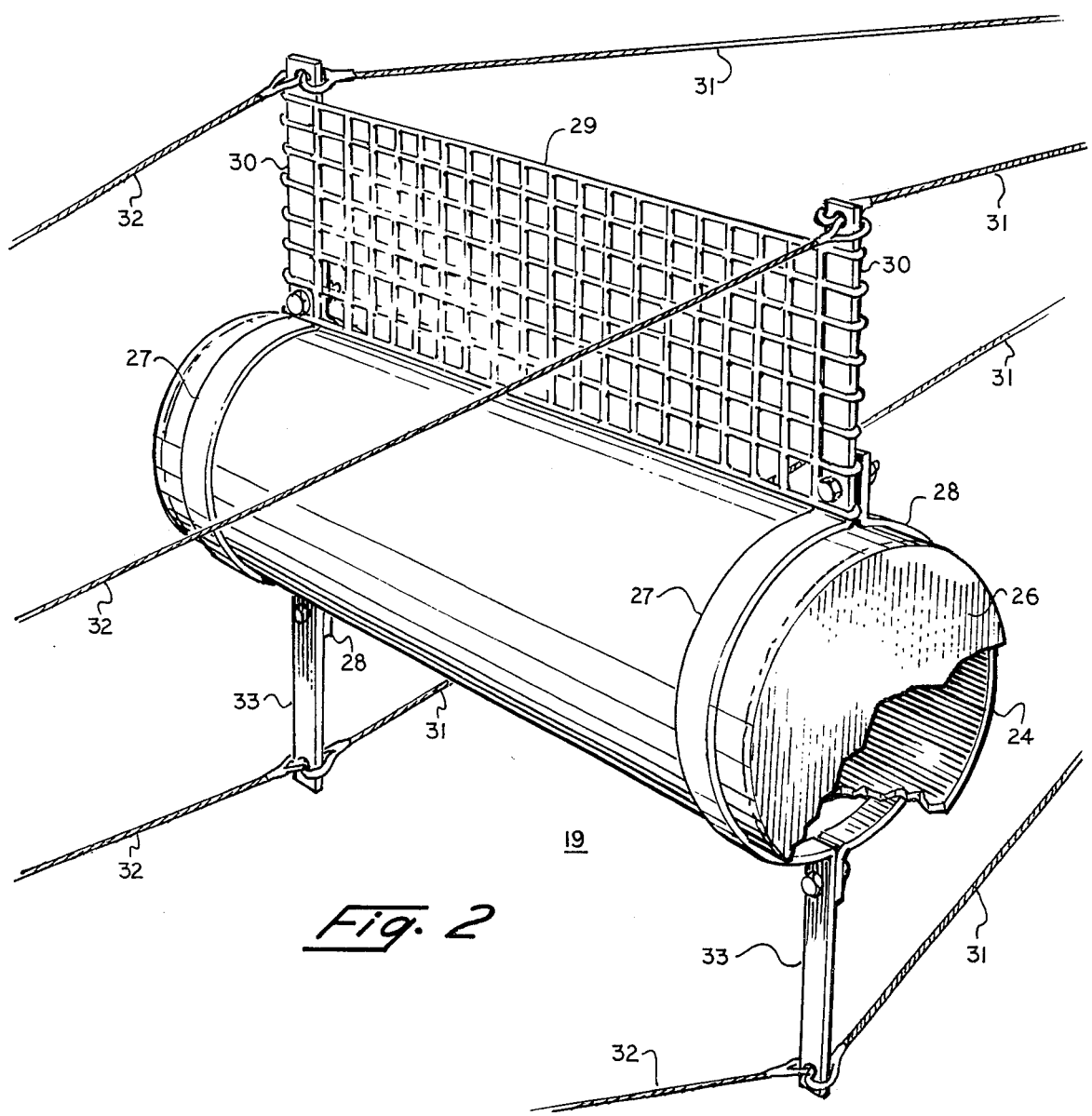
FIG. 2 is a three-dimensional view with portions broken away of the scum drag of FIG. 1, showing the detailed construction.

Referring now to FIG. 2, the float for the scum drag 9 may consist of a hollow steel pipe 24 to which end caps 26 are welded at each end. Semicylindrical clamp members 27 are disposed about the ends of the drum 24 and have integrally formed upwardly-extending posts 30 and downwardly-extending integral posts 33. A semicylindrical clamp member 28 engages the bottoms of the posts 30 and 33 to secure them to the drum 24.

Secured between the upwardly-extending posts 30 is a fence 29, which acts as a rake as seen in FIG. 1 for the engagement of the floating scum and moving it in the direction of movement of the drum 24. Connected to the ends of each of the posts 30 and 33 are harness draglines 31 connected to the dragline 21 for movement of the float-fence combination to the right. Connected to the ends of the posts 30 and 33 are harness draglines 32, which connect these posts to the left dragline 23, as shown in FIG. 1. The fence 29 is preferably made of stout wire, and the wire may be wrapped around the post 30 for securing the fence thereto.

The operation may best be illustrated by FIG. 1. During normal methane generation the level of the pool 16 is higher than that shown, and the scum removal openings 12 and 13 are normally closed by gas-tight doors. The scum width, accordingly, is less than the diameter of the shell 11, and the float 24 is at a point above the center line of the shell 11. When it is desired to remove the accumulated scum, which may occur every few months or as infrequently as one year depending upon the scum accumulation, the outlet 18 is operated to drop the level of the pool 16 to that illustrated in FIG. 1. The scum drag 19 is preferably positioned to the far left in FIG. 1 during normal methane operation. The dragline 21 is preferably a steel rod, which is allowed to drop to the bottom of the shell 11 during normal operation. This dragline 21 is thereupon manually fished out of the bottom of the shell 11 and connected to a suitable rope, which in turn may be connected to a truck or tractor. The dragline 21 is then pulled to the right, as seen in FIG. 1, causing the scum pile 22 to be pushed to the right also. When this scum pile 22 reaches the scum opening 13, it is pulled through that opening and dumped into a truck or other suitable means of conveying it away from the digester or generator.

Various materials of construction can be used for the scum drag illustrated. The harness draglines 31, for example, may be steel rods welded to the dragline 21, and these may be sufficient to maintain the entire scum float 19 in an upright position illustrated during normal operation of the methane generator. The return harness lines 32 may be wire rope, and these may be fished out of the bottom of the shell 11 also to be connected to the dragline 23 for returning the float to the left-hand end of the shell 11.

Various modifications will occur to those skilled in the art, and the drawings are illustrative only and represent the presently preferred embodiment of the invention, as required by the rules of the Patent and Trademark Office. Accordingly, the following claims include within their scope all modifications and variations that fall within the true spirit and scope of the invention.

I claim:

1. In combination with an enclosed elongated tank for use as a methane generator normally having a liquid pool therein, having parallel side walls at the pool surface, and having an apertured front-end wall at one end of the pool and an apertured rear-end wall at the other end of the pool, a scum drag comprising:
    a. a transverse float having a dimension transverse to the elongated tank substantially the same as the transverse dimension of the surface of the liquid pool and having a front toward the front-end wall and a rear toward the rear-end wall of the tank;
    b. a vertical fence secured to the top of the float;
    c. a front drag line connected to the float on the front side of the float and operable through the aperture in the front-end wall to move the float along the length of the pool in one direction;
    d. and a rear drag line connected to the float on the rear side of the float and operable through the aperture in the rear-end wall to move the float along the length of the pool in the other direction; whereby any scum accumulated on the surface of the pool may be removed by pulling one drag line in one direction through the aperture in one wall and returning the drag to a rest position by pulling the other drag line in the other direction through the aperture in the other wall, said scum being removable.

* * * * *